United States Patent [19]
Wakiyama

[11] Patent Number: 5,453,616
[45] Date of Patent: Sep. 26, 1995

[54] PROBE MICROSCOPE HAVING ERROR CORRECTION PIEZOELECTRIC SCANNER

[75] Inventor: Shigeru Wakiyama, Chiba, Japan

[73] Assignee: Seiko Instruments, Inc., Japan

[21] Appl. No.: 324,740

[22] Filed: Oct. 18, 1994

[51] Int. Cl.[6] ................................................ H01J 37/26
[52] U.S. Cl. ............................................ 250/306; 73/105
[58] Field of Search ................................. 250/306, 307; 73/105; 369/126

[56] References Cited

U.S. PATENT DOCUMENTS 5,260,926  11/1993  Kuroda et al. ........................... 250/306
5,308,974  5/1994  Elings et al. ............................. 250/306
5,349,735  9/1994  Kawase et al. ........................... 250/306

Primary Examiner—Jack I. Berman
Assistant Examiner—James Beyer
Attorney, Agent, or Firm—Adams & Wilks

[57] ABSTRACT

By indirectly measuring the movement of a first scanner comprising a piezoelectric element which moves a specimen or a detecting part by providing a second scanner separate from the first scanner and disposing a displacement detecting sensor in the vicinity of the second scanner and causing the second scanner to move in a similar way as the first scanner, the error between the results after image processing and the actual shape, coming from the non-linearity between the impressed voltage and the amount of displacement of the piezoelectric element, is reduced.

4 Claims, 7 Drawing Sheets

PROBE MICROSCOPE HAVING ERROR CORRECTION PIEZOELECTRIC SCANNER

BACKGROUND OF THE INVENTION

This invention relates to a probe microscope for analyzing the surface state of a material by detecting interatomic forces (AFM: Atomic Force Microscope) or magnetic forces (MFM: Magnetic Force Microscope) acting between materials or tunnel currents (STM: Scanning Tunneling Microscope) occurring between materials.

Since being devised by G. Binning et al (Physical Review Letter Vol. 56 p. 930 1986), the atomic force microscope (AFM), which is a type of probe microscope, has been considered promising as new means for observing surface shapes of insulating materials, and research into these microscopes has been being advanced. This AFM will be discussed as an example. Among AFMs there are types for use with relatively small specimens which scan the specimen side over a plane with respect to a detecting part and types for use with large specimens which scan a detecting part with respect to the surface of the specimen; FIG. 7 is a block diagram of a type wherein the detecting part is scanned with respect to the specimen. This apparatus will now be described with reference to FIG. 7.

A machine section is disposed on an anti-vibration bed 1 which dampens vibrations coming from the floor; the machine section has a stage 4 by which coarse positioning in three dimensions (X, Y, Z) of a specimen 3 is performed with a box frame 2 as a reference, and a detecting part 5 is mounted via a scanner 6 on the box frame 2 facing the specimen 3. The scanner 6 moves in three dimensions and based on X, Y scanning signals from an X, Y scanning system 7 scans the detecting part 5 over the specimen 3 in the X, Y plane. The detecting part 5 consists of a device for optically measuring interatomic forces acting between the specimen 3 and a detecting chip with a sufficiently sharpened end as displacements of a spring element 71 on which the detecting chip is mounted. The Z axis of the scanner 6 is operated by a Z follow-up signal outputted by a Z axis servo system 10 so as to keep the value of a detection part signal 9 outputted by the detecting part 5 constant at all times. The Z axis follow-up signal and the X, Y axis scanning signals are processed through image processing means (a computer) 12 and displayed on a monitor 13.

Conventionally the scanner 6 consists of a piezoelectric element. As shown in FIG. 5, a piezoelectric element 51 is deformed by a voltage being impressed on electrodes 52 disposed on both sides of it and can be made to extend and contract by the direction of the impressed voltage being changed relative to the direction of polarization of the piezoelectric element. Normally, PZT (titanium lead zirconate) is mainly used as the material of the piezoelectric element. As shown in FIG. 6, the displacement of this PZT piezoelectric element with respect to the impressed voltage is non-linear (has hysteresis). As a result, to cause a displacement 2L twice the size of a certain displacement L does not necessarily require twice the voltage. In the terms of FIG. 6, $V_b \neq 2 V_a$.

Consequently, because in the AFM system both the X,Y scanning signal 8 and the Z follow-up signal 11 used in the image processing are voltage values, an error occurs with respect to the actual specimen shape. Here, because the voltage variations of the X and Y axes are fixed, the error in these directions can to some extent be corrected by computation; however, correction of the Z axis which is varied irregularly by the specimen surface is more difficult than correction of the X and Y axes.

To solve this problem, it is possible to reduce the error by measuring the amount of displacement with other detecting means and performing image processing based on those values. However, in types such as the AFM system described above which measure especially large specimens, because this involves further incorporating a separate displacement detecting means onto the end portion of the scanner 6 where the detecting means 5 is disposed, severe restrictions are placed on the form of the separate displacement detecting means (it must be extremely small).

This invention has as an object the provision of a probe microscope wherein separate displacement detecting means is used as means for reducing the error, coming from the non-linearity of the piezoelectric element, between the results after image processing and the actual shape, of a constitution having means for incorporating this displacement detecting means into the system without there being restrictions on its form such as that it must be made extremely small.

SUMMARY OF THE INVENTION

In order to solve the above problems, in this invention, a probe microscope having a detecting part for detecting a physical quantity occurring as a result of an interaction between a probe and the surface of a specimen, a first scanner comprising a coarse movement mechanism for three dimensionally moving the specimen and the detecting part relatively and a piezoelectric element, Z axis controlling means for based on information from the detecting part applying a Z follow-up signal to a Z axis electrode of the first scanner so as to maintain a fixed distance between the specimen and the detecting part, X, Y scanning means for applying X, Y scanning signals to X, Y axis scanning electrodes of the first scanner and causing the scanner to scan in the X, Y directions, image processing means for inputting and performing image processing on the Z axis follow-up signal and the X, Y scanning signals, and image display means for displaying the shape of the surface of the specimen based on information from the image processing means, is characterized in that it has at least one second scanner means for detecting the displacement of the second scanner and the second scanner is operated by the Z axis follow-up signal being applied to the second scanner also and a displacement detection signal from the displacement detecting means is inputted into the image processing means and the shape of the surface of the specimen or a physical quantity is displayed based on the displacement detection signal.

With this invention, by use of the above means, it is possible to measure the movement of the first scanner indirectly and reduce the error, coming from the non-linearity between the impressed voltage and the displacement of the piezoelectric element used in the first scanner, between the results after image processing and the actual shape. Also, because the other detecting means need not be disposed in the vicinity of the detecting part of the probe microscope, it is possible to ease the form restrictions on the other detecting means.

DETAILED DESCRIPTION OF THE INVENTION

Embodiments of the invention will now be described with reference to the accompanying drawings.

(Embodiment 1)

Figure 1:
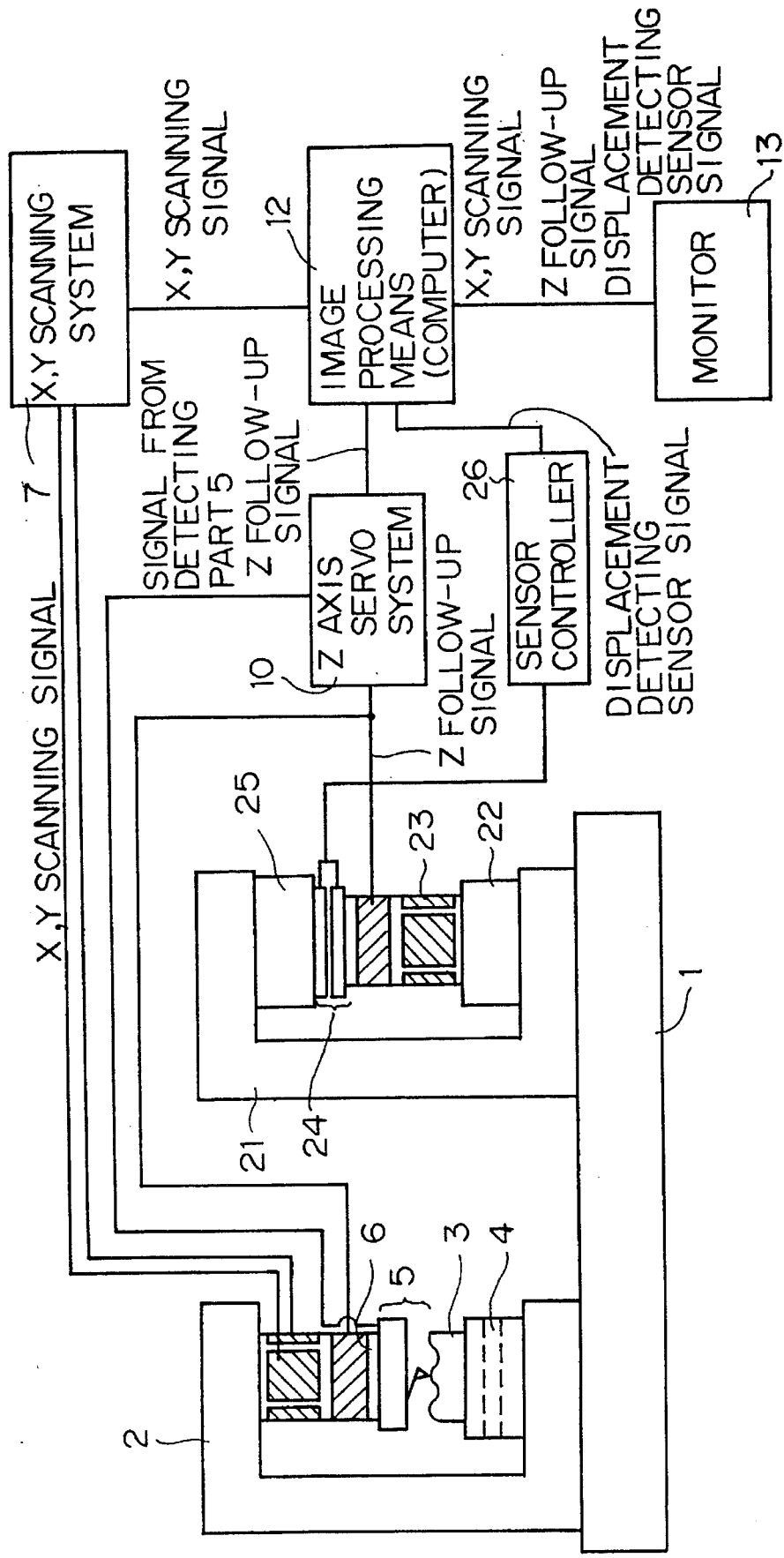
FIG. 1 is a block diagram showing a first embodiment of the invention.

FIG. 1 is a block diagram showing a first embodiment of the invention. The basic probe microscope constitution shown in the prior art, an anti-vibration bed 1, a box frame 2, a specimen 3, a stage 4, a detecting part 5, a scanner 6, an X, Y scanning system 7, a Z axis servo system 10, an image processing means (computer) 12, and a monitor 13, is provided. A scanner 23 which moves in the similar way as the scanner 6 (the same amount of movement in the Z axis direction as the scanner 6, or a fixed multiple thereof) is mounted via a Z coarse movement mechanism 22 on the anti-vibration bed 1 with a box frame 21 as a base. Also, an attitude adjustment mechanism 25 for a displacement detecting sensor 24 is mounted on the box frame 21. In other words, the displacement detecting sensor 24 is disposed between the attitude adjustment mechanism 25 and the scanner 23 and only the Z axis is corrected. In this embodiment a capacitance-type displacement gauge is used but other displacement gauges, for example displacement gauges based on optical means, can of course be used. Because the measurable range of the capacitance-type displacement gauge used in this invention is limited by the distance between two facing electrodes, the Z coarse movement mechanism 22 and the attitude adjustment mechanism 25 are operated and adjusted in that range.

The wiring is such that the same Z follow-up signal impressed on the Z axis movement electrodes of the scanner 6 are impressed on the Z axis movement electrodes of the scanner 23. As a result of this the Z axis of the scanner 6 and the Z axis of the scanner 23 move similarly. In other words, by measuring the movements on the Z axis of the scanner 23, the movements on the Z axis of the scanner 6 can be measured indirectly. Accordingly, this scanner 23 movement is measured using the displacement detecting sensor 24, and a displacement detecting sensor signal 27 outputted through a sensor controller 26 is inputted into the image processing means (computer) 12 and turned into an image. In this way it is possible to reduce the error, coming from the non-linearity of the piezoelectric element, between the results after image processing and the actual shape compared with the conventional case where image processing was carried out using the Z follow-up signal 11.

In the above embodiment it was a type for use with large specimens in which a detecting part moves and scans the surface of a specimen that was discussed, but naturally the embodiment can also be used in a type for use with relatively small specimens in which the specimen moves and scans a detecting part in a plane direction.

(Embodiment 2)

Figure 2:
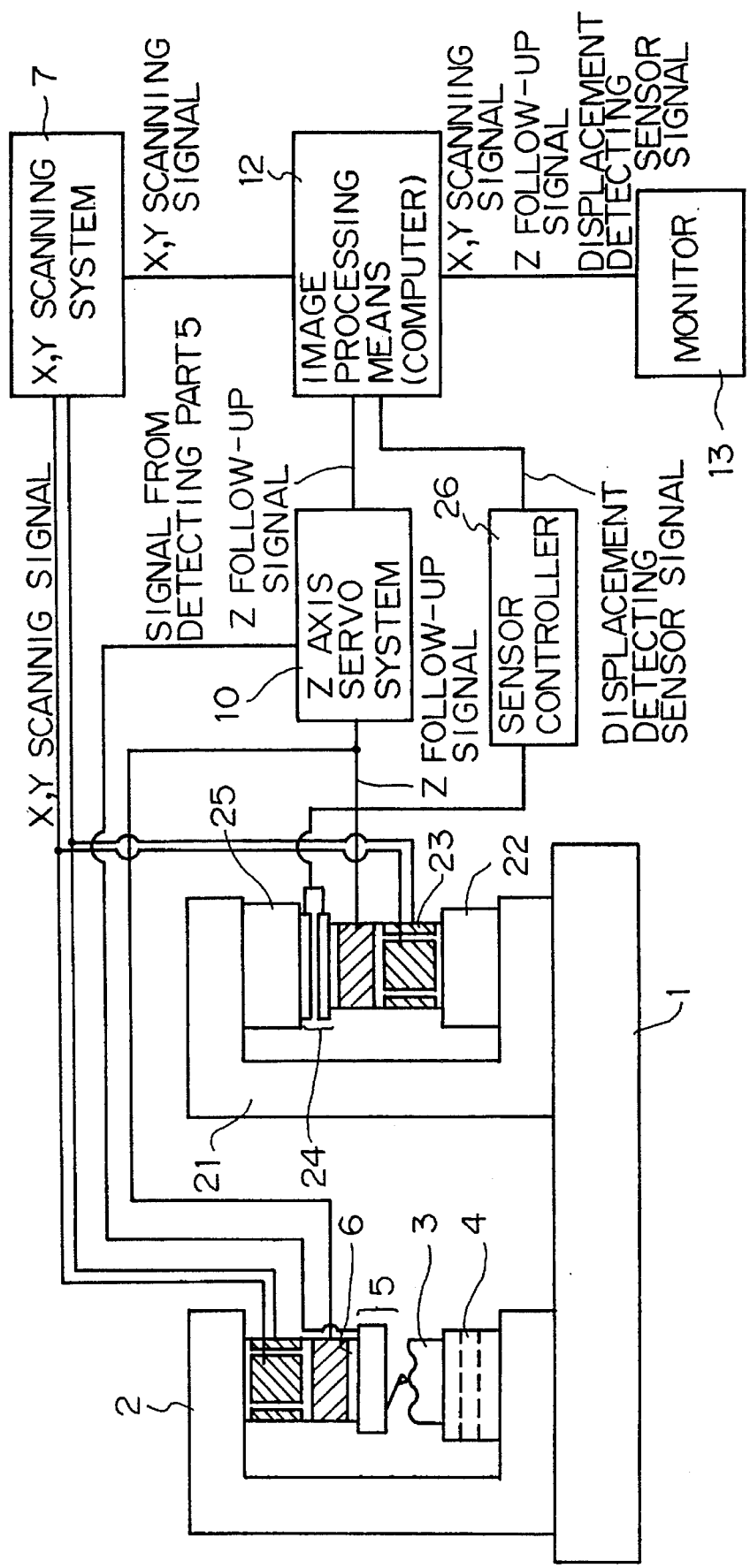
FIG. 2 is a block diagram showing a second embodiment of the invention.

FIG. 2 is a block diagram showing a second embodiment of the invention. The scanners 6, 23 used in the first embodiment are of hollow cylindrical type and bimolph type so that the movement in the X, Y plane is effected by a neck oscillation action; because of this, there is interference to the Z axis caused by the X, Y movement. This is normally a relatively small value of about 0.1% at the most of the amplitude of the oscillation, but to reduce the error arising from this point in this embodiment the X Y signal from the X, Y scanning system 7 is impressed on X, Y electrodes of the scanner 23 so that in the plane also the scanner 23 is made to move in similar way as the scanner 6. In the rest of its constitution this embodiment is as discussed in the first embodiment. Naturally, similar effects are obtained.

(Embodiment 3)

Figure 3:
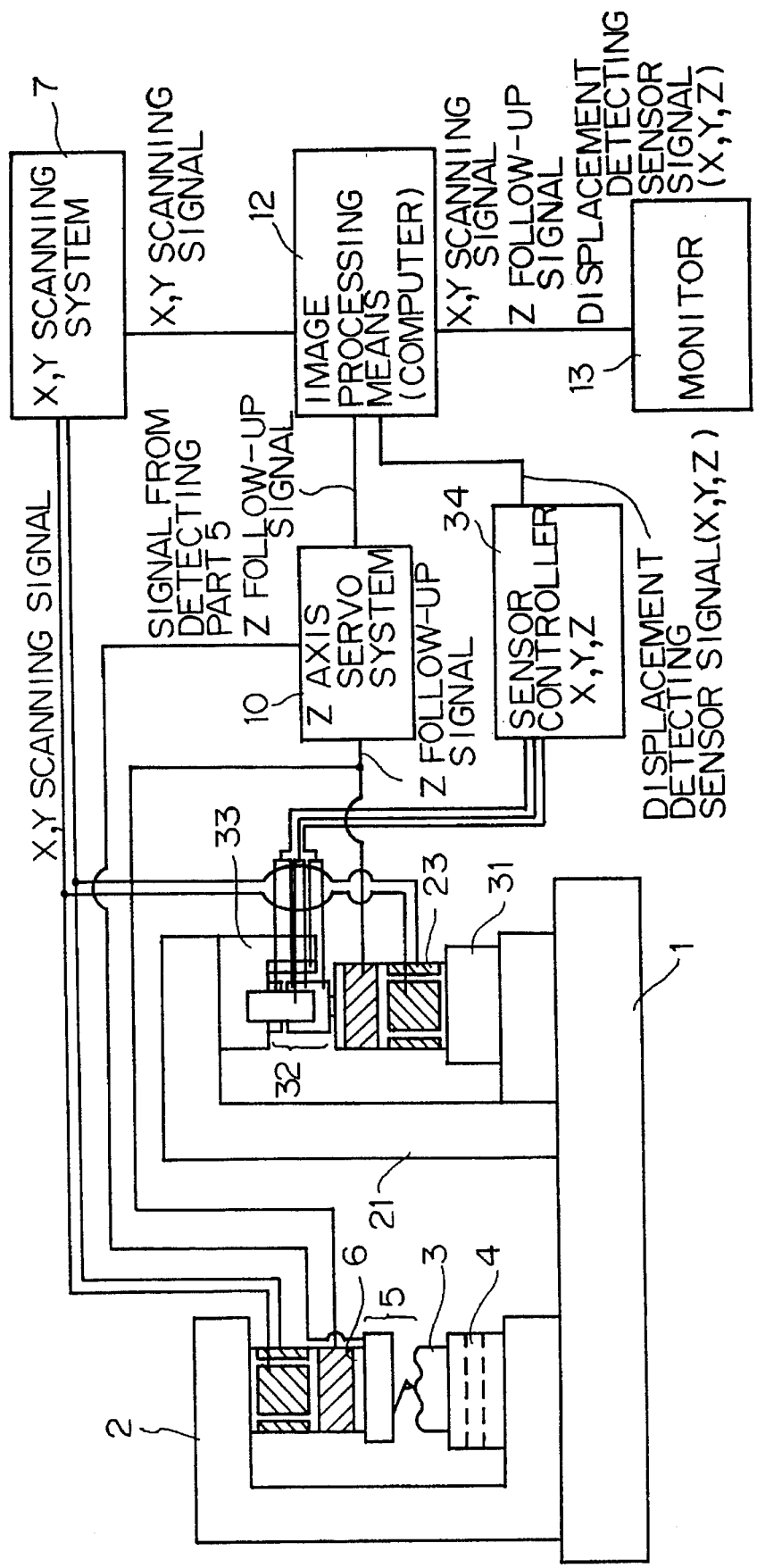
FIG. 3 is a block diagram showing a third embodiment of the invention.

FIG. 3 is a block diagram showing a third embodiment of the invention. This embodiment is an example in which, whereas in the above first and second embodiments what was corrected was the Z axis only, the X and Y axes are added and correction of 3 axes is performed. First, the anti-vibration bed 1, the box frame 2, the specimen 3, the stage 4, the detecting part 5, the scanner 6, the X, Y scanning system 7, the Z axis servo system 10, the image processing means (computer) 12 and the monitor 13 shown in the prior art are provided as they were in the first and second embodiments. A scanner 23 which moves in the similar way as the scanner 6 is mounted via a stage 31 movable on 3 axes with a box frame 21 as a reference on the anti-vibration bed 1. An attitude adjustment mechanism 33 of a displacement detecting sensor 32 which detects 3 axial directions is mounted on the box frame 21. In this embodiment also a static capacitance-type displacement gauge is used, and as was discussed in the first embodiment the gap between the 2 electrodes of the sensor is adjusted by operation of the stage 31 and the attitude adjustment mechanism 33.

The displacement detecting sensor 32 measures the displacements (X, Y, Z) of the scanner 23 which is moved by the X Y scanning signal 8 and the Z follow-up signal 11. A displacement detecting sensor signal (X, Y, Z) 35 measured using the displacement detecting sensor 32 and outputted through a sensor controller 34 is inputted into the image processing means (computer) 12 and turned into an image. In this way it was possible to reduce the error, coming from the non-linearity of the piezoelectric element, between the results after image processing and the actual shape on all 3 axes more than in the case wherein the X Y scanning signal 8 and the Z follow-up signal 11 were used for the image processing.

(Embodiment 4)

Figure 4:
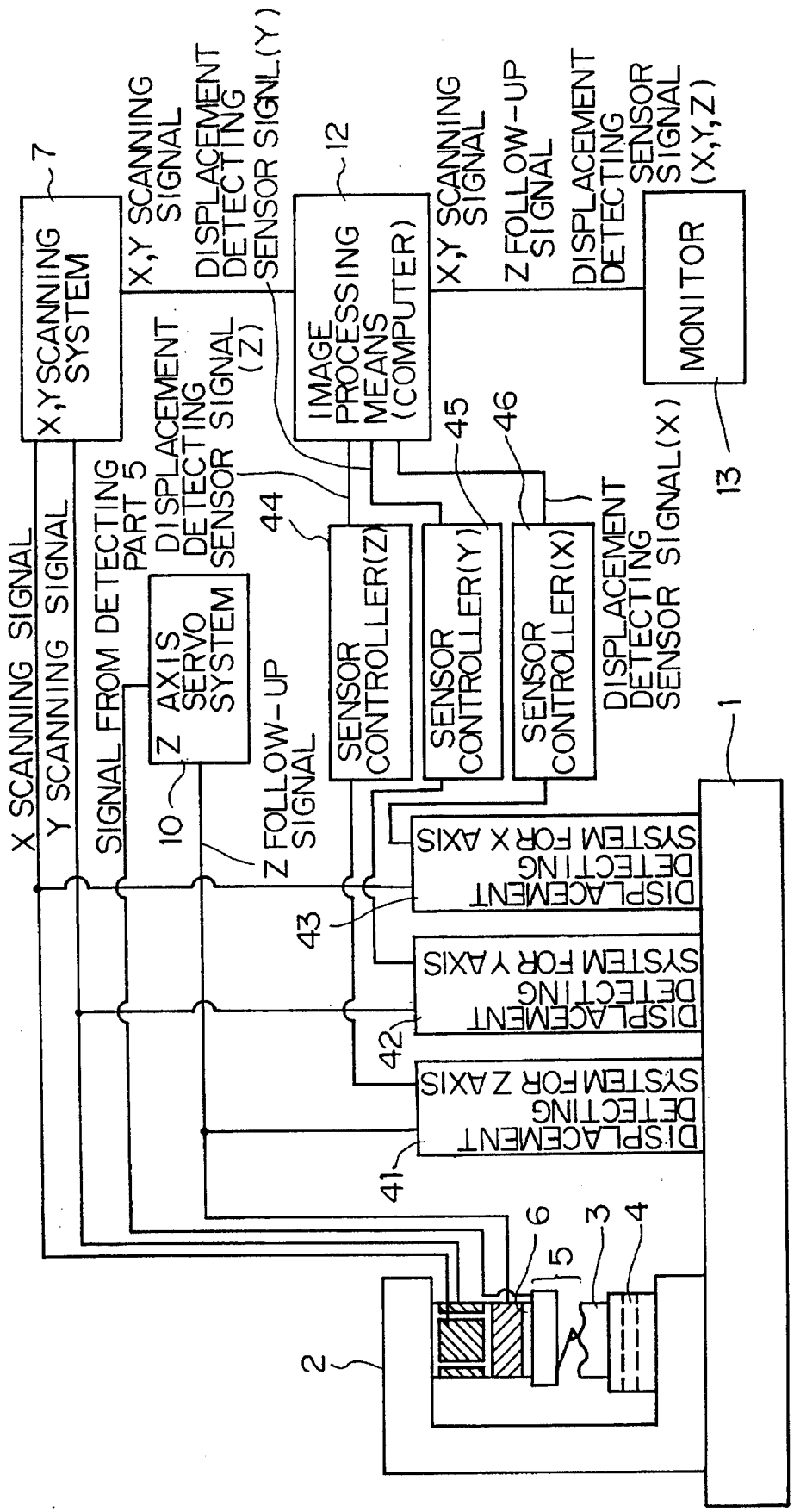
FIG. 4 is a block diagram showing a fourth embodiment of the invention.
Figure 5:
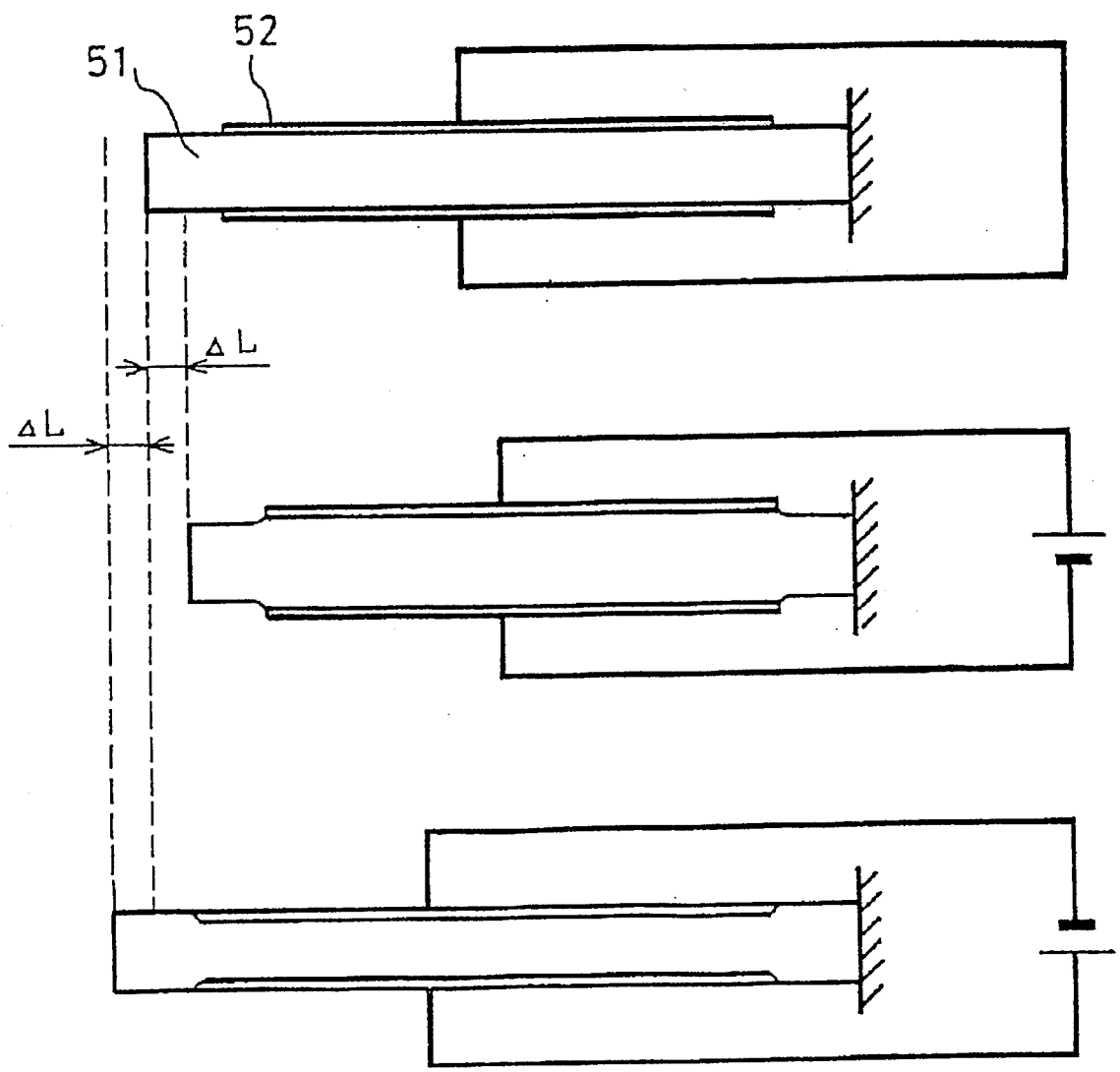
FIG. 5 Is a view showing deformation of a piezoelectric element.
Figure 6:
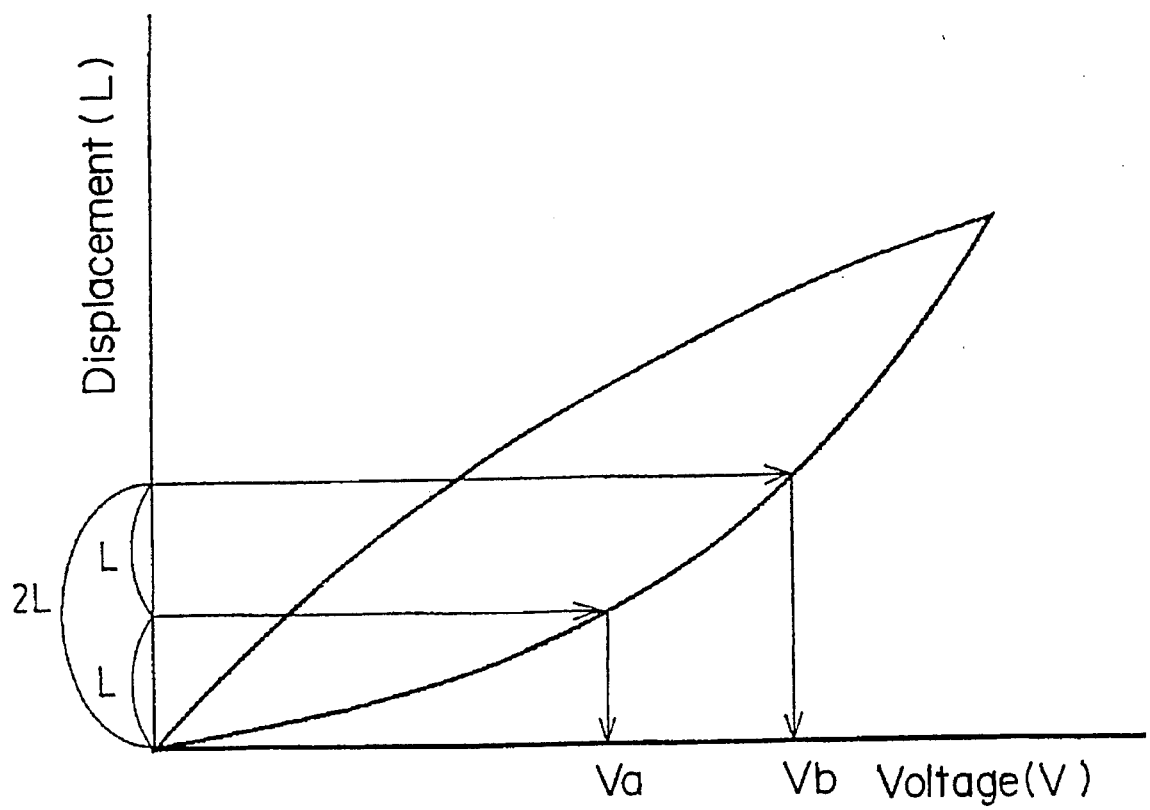
FIG. 6 is a view illustrating the non-linearity of a piezoelectric element.
Figure 7:
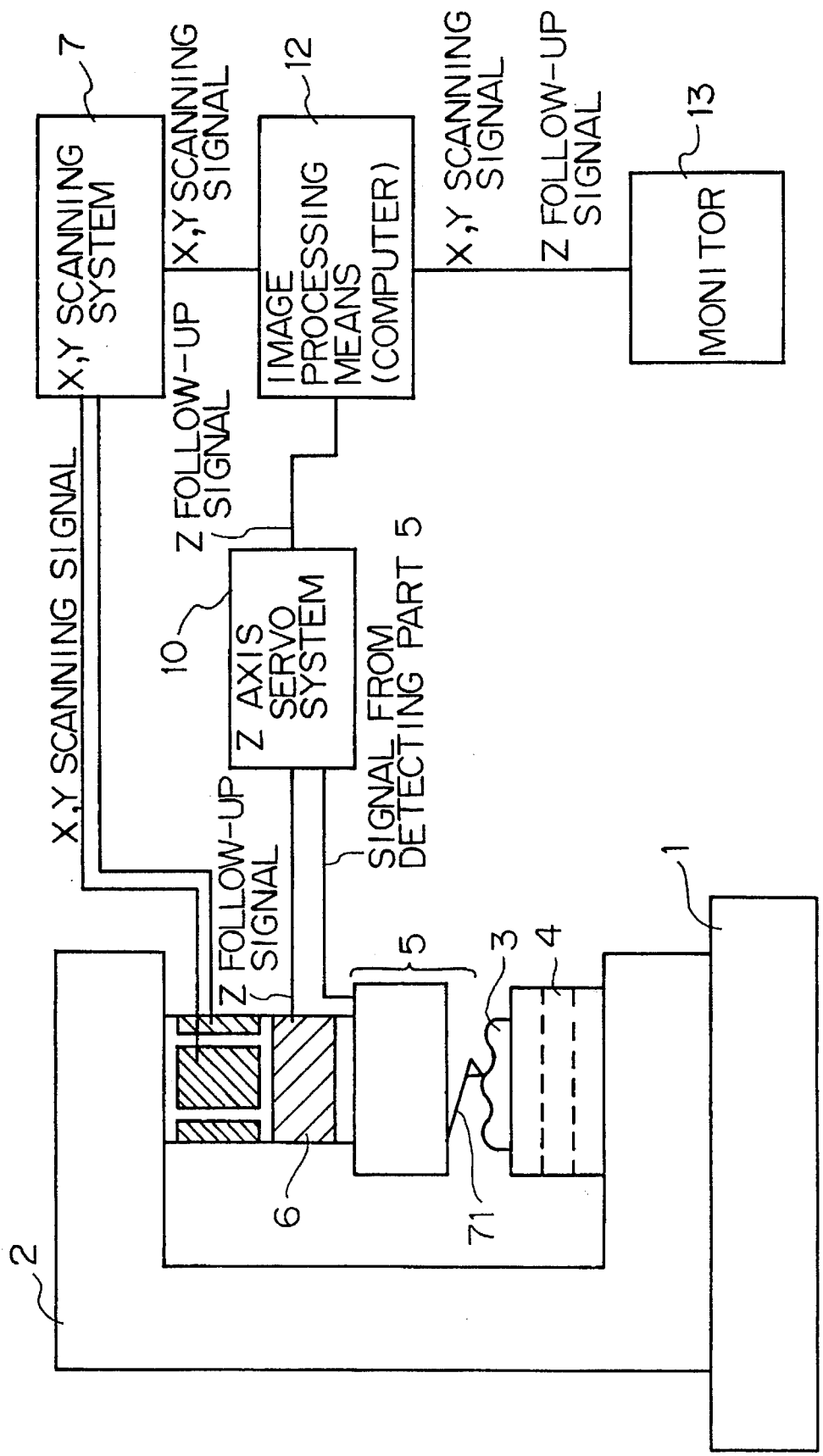
FIG. 7 is a block diagram of a conventional AFM type which scans a detecting part with respect to a specimen surface.

FIG. 4 is a block diagram of a fourth embodiment of the invention. This embodiment like the third embodiment illustrates means for performing correction for 3 axes (X, Y, Z). In the above third embodiment because 3 axes were disposed on the scanner 23, depending on the form of the displacement detecting sensor in some cases it is difficult to incorporate the sensor. As means for solving this problem the construction has a displacement detecting system like that shown in the first embodiment having a sensor and a displacement detecting sensor for each axis: a displacement detecting system 41 for the Z axis, a displacement detecting system 42 for the Y axis and a displacement detecting system 43 for the X axis. Displacement detection signals (X, Y, Z) 47, 48 and 49 outputted through sensor controllers 44, 45 and 46 of the respective axes are inputted into the image processing means (computer) 12 and turned into images. In this way, like in the third embodiment, it was possible to reduce the error, coming from the non-linearity of the piezoelectric element, between the results after image processing and the actual shape on all 3 axes more than in the case wherein the X Y scanning signal 8 and the Z follow-up signal 11 were used for the image processing.

Because with this invention displacement correction means can be constituted as a system without other displacement detecting means being disposed in the vicinity of the scanner of the probe microscope proper, there is the effect that it is possible to ease the restrictions on the form of the displacement detecting means.

What is claimed is:

1. In a probe microscope having a detecting part for detecting a physical quantity occurring as a result of an interaction between a probe and the surface of a specimen, a first scanner comprising a piezoelectric element and a coarse movement mechanism for three-dimensionally moving said specimen and said detecting part relative to each other, Z axis controlling means for, based on information from said detecting part applying a Z follow-up signal to a Z axis electrode of said first scanner so as to maintain a fixed distance between said specimen and said detecting part, X, Y scanning means for applying X, Y scanning signals to X, Y axis scanning electrodes of said first scanner and causing said first scanner to scan in the X, Y directions, image processing means for inputting and performing image processing on said Z axis follow-up signal and said X, Y scanning signals, and image display means for displaying the shape of the surface of said specimen based on information from said image processing means, said probe microscope characterized in that it has further at least one second scanner and displacement detecting means for detecting the displacement of said second scanner, said second scanner being operated by said Z axis follow-up signal being applied to said second scanner as well as to said first scanner, and a displacement detection signal from said displacement detecting means being inputted into said image processing means so that the shape of the surface of said specimen or a physical quantity may be displayed based on said displacement detection signal.

2. A probe microscope according to claim 1, wherein said first scanner and said second scanner move similarly.

3. A probe microscope according to claim 1, wherein said X, Y scanning signals are further applied to said second scanner.

4. A probe microscope according to claim 2, wherein said X, Y scanning signals are further applied to said second scanner.

* * * * *